United States Patent
Reeves et al.

[11] Patent Number: 5,807,268
[45] Date of Patent: Sep. 15, 1998

[54] DISPOSABLE SENSING DEVICE WITH CONTANEOUS CONFORMANCE

[75] Inventors: William Reeves, New Haven; Christian Hilmer, Essex; Douglas R. Miller, Westport, all of Conn.

[73] Assignee: MedAcoustics, Inc., Raleigh, N.C.

[21] Appl. No.: 733,767

[22] Filed: Oct. 18, 1996

Related U.S. Application Data

[62] Division of Ser. No. 247,761, May 23, 1994, abandoned, which is a continuation of Ser. No. 942,286, Sep. 9, 1992, Pat. No. 5,365,937.

[51] Int. Cl.⁶ ............................................. A61B 5/02
[52] U.S. Cl. ...................... 600/528; 600/527; 600/513; 600/514
[58] Field of Search ..................... 128/695 R, 701, 128/700, 714, 715, 662.01–662.06; 600/457, 458, 461–469, 449, 513, 514, 527, 528

[56] References Cited

U.S. PATENT DOCUMENTS

| | | | |
|---|---|---|---|
| 477,961 | 10/1892 | Saltzman | 128/715 |
| 3,573,394 | 4/1971 | Birnbaum | 128/715 |
| 4,792,145 | 12/1988 | Eisenberg et al. | 128/715 |
| 4,803,996 | 2/1989 | Peel et al. | 128/715 |
| 4,805,633 | 2/1989 | Kotani et al. | 128/715 |
| 4,840,183 | 6/1989 | Takashi et al. | 128/715 |
| 4,947,859 | 8/1990 | Brewer et al. | 128/715 |
| 5,002,058 | 3/1991 | Martinelli | 128/662.06 |
| 5,315,512 | 5/1994 | Roth | 128/660.07 |
| 5,365,937 | 11/1994 | Reeves et al. | 128/715 |
| 5,598,845 | 2/1997 | Chandraratna et al. | 128/662.03 |

*Primary Examiner*—Jennifer Bahr
*Assistant Examiner*—Stephon Huang
*Attorney, Agent, or Firm*—Edward S. Irons

[57] ABSTRACT

The present invention relates to a sensing device for capturing acoustic heart sounds. The sensing device has a diaphragm formed from a piezoelectric transducer material which generates excitation signals in response to acoustic and vibratory energy outputs. The sensing device includes metallization layers on the diaphragm for receiving and transmitting the excitation signals to an output display device via associated electrical contacts and electrical leads and also includes a layer of adhesive material for coupling the sensing device to the subject. The sensing device further includes snap connectors for allowing the device to be quickly disengaged from electrical leads and discarded. A patch sensor device is disclosed which enables acoustic outputs to be triangulated and pinpointed.

3 Claims, 5 Drawing Sheets

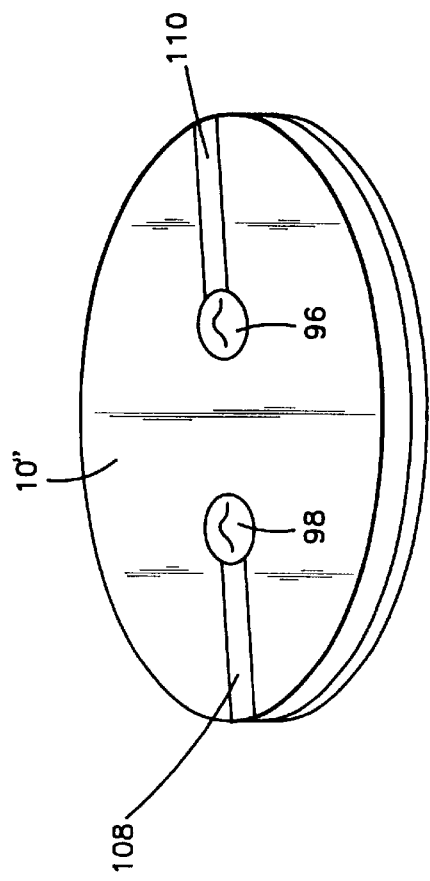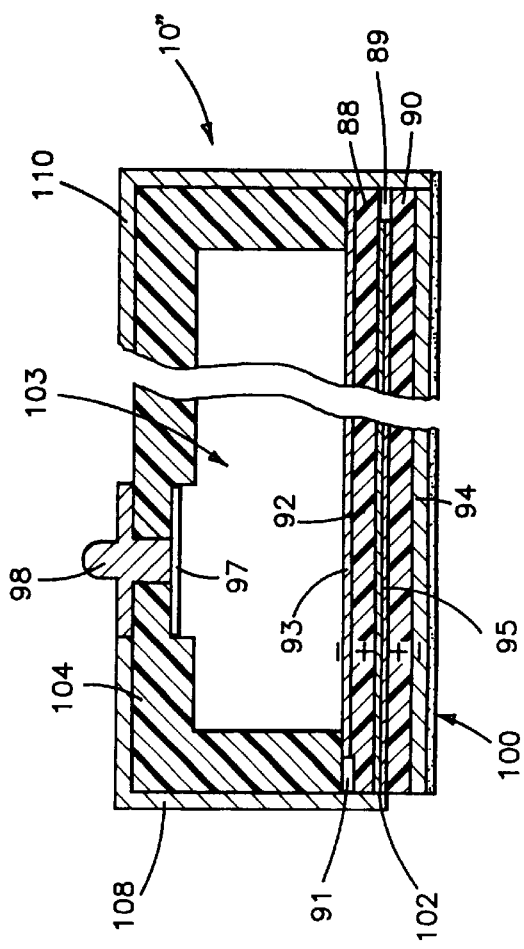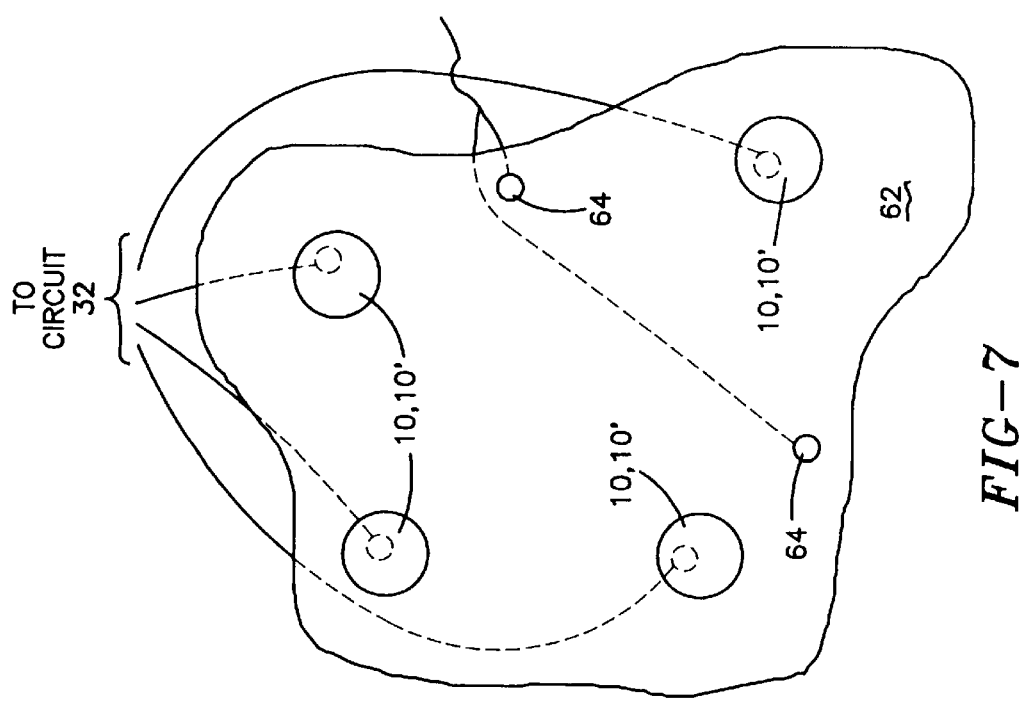

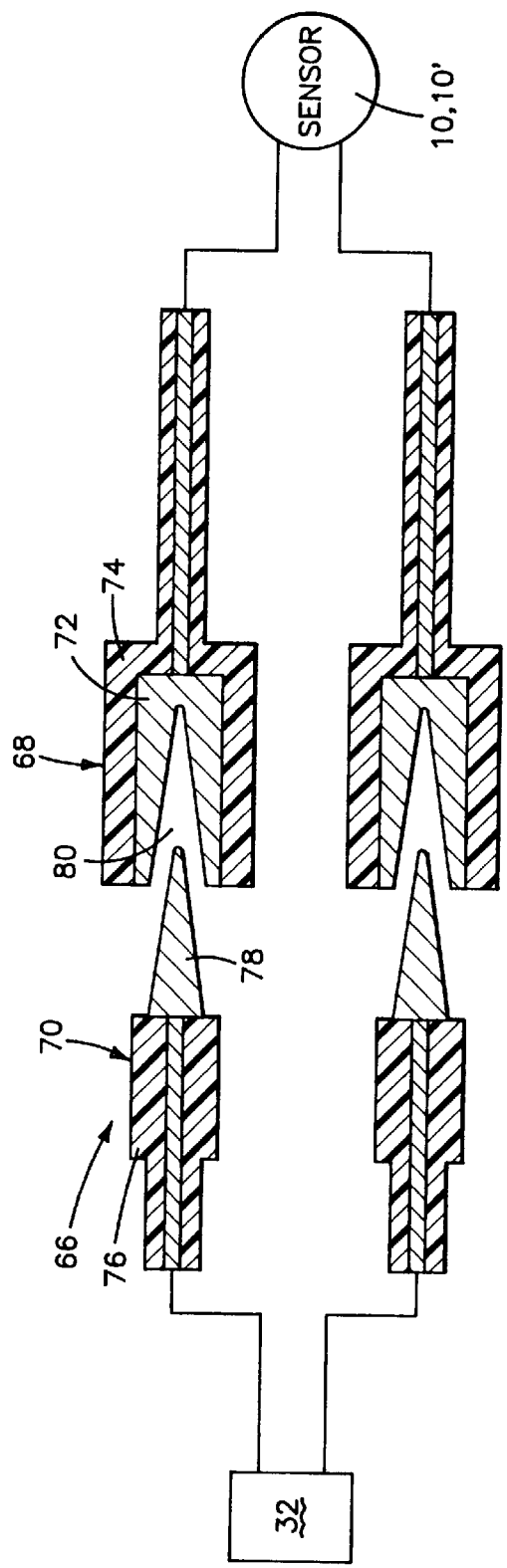
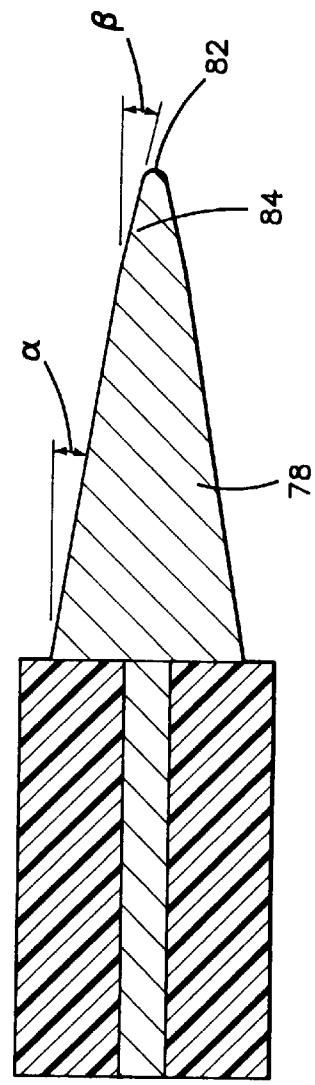
FIG-8
FIG-9

DISPOSABLE SENSING DEVICE WITH CONTANEOUS CONFORMANCE

This is a division of application Ser. No. 08/247,761 filed May 23, 1994, now abandoned, which is a continuation of Ser. No. 07/942,286 filed Sep. 9, 1992, now patent 5,365,937 issued Nov. 22, 1994.

BACKGROUND OF THE INVENTION

The present invention relates to an improved sensing device for capturing cardiac output (S1 and S2) and acoustic and vibratory outputs from arterial blood flow off the chest and appendages.

There are many types of sensors, transducers and pickups used in general industrial applications. Several are specifically designed to capture heart sounds and body noises. One such sensor or pickup for heart sounds is a condenser microphone. This type of microphone is specifically designed for 2-D phonocardiography systems for capturing heart sounds off the human chest for interpretation.

Other prior art devices include accelerometers and piezoelectric crystal devices for capturing low frequency vibrations off the human chest as an indication of heart muscle damage. Apexcardiography, vectorcardiography and seismocardiograph equipment all use probes to capture signals off the flesh.

One of the inherent drawbacks of these prior art devices is the fact that they rely on rigid metal or ceramic sensors which do not conform to the curves, appendages and/or body hair of a subject. This makes any type of integral mechanical coupling very difficult. As a result, the efficiency and thus the accuracy of the sensor is greatly diminished and critical heart sound energy, which is an integral part of the detection and diagnosis of heart disease, is lost.

Some prior art sensors, for this purpose and other industrial applications, are formed by accelerometers and piezoelectric crystals epoxied onto appendages of the body. None of these sensors however has a desirable set of pliable conformance characteristics. Still further none of these known sensors utilize quick connect and disconnect leads on the sensor for electrical lead connection.

Accordingly, it is an object of the present invention to provide a sensing device for capturing acoustic and vibratory energies, caused by turbulent blood flow through major vessels, the heart and its valves, and muscle disfunction of the heart, off the flesh of a subject.

It is a further object of the present invention to provide a sensing device as above having a set of pliable conformance characteristics for coupling the sensing device to the flesh for maximum energy transfer.

It is yet a further object of the present invention to provide a sensing device as above which can be sterilized and which has utility in operating rooms, intensive care units, and other environments where sterility is critical.

It is still another object of the present invention to provide a sensing device as above which can be quickly connected and disconnected from electrical leads to create an easily disposable sensing device that can be used once and discarded.

Still other objects and advantages of the present invention are set forth in the following description and drawings wherein like reference numerals depict like elements.

SUMMARY OF THE INVENTION

The foregoing objects and advantages are attained by the sensing device of the present invention which is capable of capturing acoustic and vibratory energies. In accordance with the present invention, the sensing device has a diaphragm formed from a thin piezoelectric polymer film transducer material, a thin film of conductive material on two surfaces of the diaphragm for receiving and transmitting excitation signals from the polymer film material, and a layer of adhesive material applied to the subject attachment side of the sensing to mechanically couple the sensing device to the subject.

In a preferred embodiment of the present invention, the diaphragm is formed by a polyvinylidene fluoride material which, with no or very little input voltage, is capable of generating its own output voltage in proportion to the excitation caused by the acoustic and/or vibratory energies. This type of material has been found to be extremely advantageous because it offers no or little possibility of a subject being shocked or burned from input voltages. Additionally, extraneous background noise is not captured as the transmission relies mainly on physical contact of the sensor to the body. This material is sufficiently flexible to allow a sensor to be formed that is flexible enough to conform with the flesh and become part of the flesh for maximum transfer of energy.

As previously mentioned, thin layers of conductive material are applied to opposed sides of the diaphragm material and terminated with electrical lead connections. In this way, a continuous sensor circuit is created.

An important and unique feature of the sensor device of the present invention is the thin layer of adhesive material which is applied to the subject attachment side of the sensing device. Preferably, an adhesive is used which has the physical properties of adhesion, viscosity, and durometer (hardness and elasticity) which create an integral mechanical bond between sensor and flesh for maximum transfer of acoustic and vibratory energies.

If desired, the sensing device of the present invention may include a backing formed from a stiff acoustic dampening material. The backing serves to insulate the sensor diaphragm from any extraneous background noises and, by virtue of this insulating effect, creates a unidirectional acoustic material pickup which receives acoustic and vibratory signals from the flesh while remaining isolated from background noise by virtue of the backing material.

An embodiment of a sensing device is disclosed which comprises an adhesive patch with an array of sensing devices for picking up multiple acoustic output and for triangulating signals to pinpoint the location and source of the acoustic output, e.g., from which human heart valve a murmur is emanating.

Yet another sensing device is disclosed which has multiple layers of the thin piezoelectric polymer film material for generating excitation signals in response to said acoustic cardiac output.

Still other features of the present invention will be described in detail in the following description and the accompanying drawings.

BRIEF DESCRIPTION OF THE DRAWINGS

FIG. 7 is a top view of a sensor array patch using the sensing devices of the present invention;

FIG. 8 is a cross sectional view of a bayonet type connector which may be used with the sensing devices of the present invention;

FIG. 9 is a cross sectional view of the male portion of the connector of FIG. 8;

FIGS. 10 and 11 illustrate yet another sensing device in accordance with the present invention.

DETAILED DESCRIPTION

Figure 1:
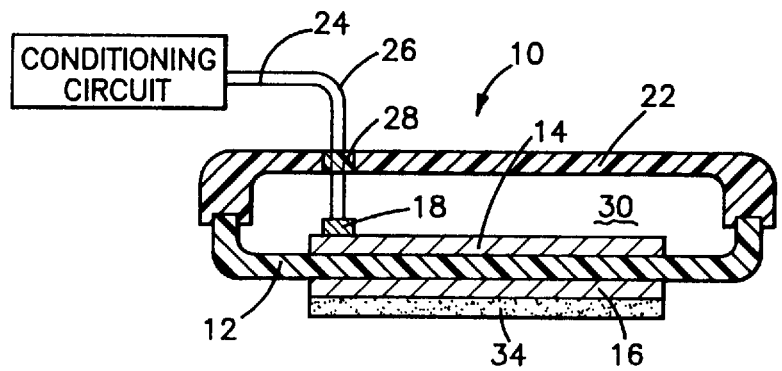
FIG. 1 is a cross sectional view of a first embodiment of a sensing device in accordance with the present invention.

Referring now to the drawings, FIG. 1 illustrates a first embodiment of a sensing device 10 in accordance with the present invention. The sensing device 10 includes a diaphragm in the form of a thin layer 12 for capturing acoustic and vibratory energies. It has been found that an improved sensing device is obtained when the layer 12 is formed from a piezoelectric polymer transducer material capable of generating its own voltage output when excited by an acoustic or vibratory output. One such material which may be used for the layer 12 is a polyvinylidene fluoride material (PVDF) sold under the trademark KYVAR by Atochem Sensors Inc. of Valley Forge, Pa.

The use of a piezoelectric polymer transducer material is advantageous because it allows a sensor to be formed which is truly non-invasive in that no energies are beamed into the subject to capture blood flow characteristics. This material allows a passive listening technique to be used. This type of material is also advantageous in that unlike an ultrasound probe, no high frequency energies have to be beamed into the subject's body and bounced off tissue and blood in order to get an indication of blood flow in arteries and through valves.

Still another advantage associated with the use of this type of material is the absence of any need to apply an excitation voltage to the material. Sensing devices formed from this material may be used with maximum safety on human subjects, including small children and infants, with no risk of electric shock or burns.

The device 10 further includes a thin film coating of metal on opposed surfaces of the polymer film material 12. The metal coatings 14 and 16 may be formed from any suitable conductive metal or metal alloy known in the art such as aluminium, nickel, copper and alloys thereof and may be applied to the surfaces of the polymer material using any suitable technique known in the art. Preferably, each layer is formed from aluminum or an aluminum alloy because such metals are inexpensive and have a relatively high impedance value.

Figure 2:
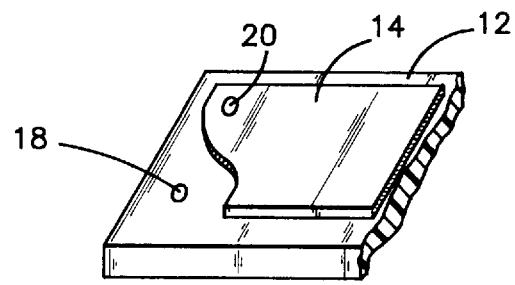
FIG. 2 illustrates a portion of a top surface of the sensor diaphragm of the sensing device of FIG. 1.

The metal coating layers 14 and 16 act as conductive surfaces for receiving and transmitting the excitation signal from the film material 12 along substantially the entire length of the film material and for transmitting excitation signals to electrical contacts or terminals 18 and 20 on the sensing device. As best shown in FIG. 2, each of the metal coating layers stops short of the edges of the polymer film material layer so as to prevent the creation of short circuits. Additionally, each of the metal coating layers 14 and 16 has one of the electrical contacts 18 and 20 associated therewith.

The terminals 18 and 20 may be any two electrical termination points located on the thin metallic films. They may be formed by solder connections, spade connections or any other type of low impedance electrical connection. At least one of the electrical terminals 18 or 20 passes through the thin film polymer material layer 12 to the thin metal layer on the opposite side.

The sensing device 10 further comprises a bow or frame 22 for stretching and holding the polymer film material 12 in tension. The bow 22 may be formed from a rigid polymer material or any other suitable non-conductive material. It may be adhesively bonded or mechanically fastened to the material 12 using any suitable means known in the art. As can be seen from FIG. 1, the bow 22 is configured so that there is an air gap 30 between it and the upper surfaces of the sensor diaphragm. If desired, the bow 22 can have a two piece construction with the thin film polymer layer 12 forming the diaphragm being positioned intermediate the two pieces.

The bow 22 acts to hold the piezoelectric film portion of the sensor in tension as a diaphragm both in the rest state and when the sensor is attached to the subject. The tension acts to create a more sensitive diaphragm out of the piezoelectric polymer transducer film as any minute acoustic or vibratory excitations are magnified by orders of magnitude. The bow or frame 22 also acts to isolate the diaphragm from extraneous noise and effectively creates a unidimensional acoustic sensor.

Two electrical leads 24 and 26 are attached to the electrical terminals 18 and 20 and are preferably of low impedance. The leads 24 and 26 may be electrically shielded, may have any desired length, and may be connected to the terminals 18 and 20 in any desired manner.

The leads 24 and 26 pass through a strain relief device 28 in the bow 22. The strain relief device and the leads can be molded into the bow or frame or may be mechanically assembled as three separate items. The strain relief device 28 may be formed by a rubber grommet or by an epoxy material.

A thin film layer 34 of peel and stick adhesive is applied to the subject side of the sensing device 10 and the bow 22. The adhesive acts to mechanically couple the sensor to the flesh in such a way that the sensor and flesh conform and become one. This insures that the maximum amount of acoustic and vibratory energy from heart valves and major arteries within the body is received by the diaphragm formed by the piezoelectric polymer material layer. The adhesive used to form the thin film layer 34 may be any suitable adhesive known in the art such as the adhesive used in a product called "Double-Stick Discs" manufactured by 3M.

The sensing device 10 may be electrically connected by the leads 24 and 26 to any suitable display device and/or microprocessor (not shown) known in the art. Before the signal from the sensor is transmitted to the display device and/or microprocessor, it may be passed through an appropriate analog conditioning circuit 32 for filtering and amplifying the output signal to rid it of extraneous background noise and to highlight the low frequency heart sounds. The circuit 32 may be any suitable conditioning circuit known in the art. One type of conditioning circuit which can be used is shown in co-pending U.S. patent application No. 07/942,438, filed on an even date herewith.

Figure 3:
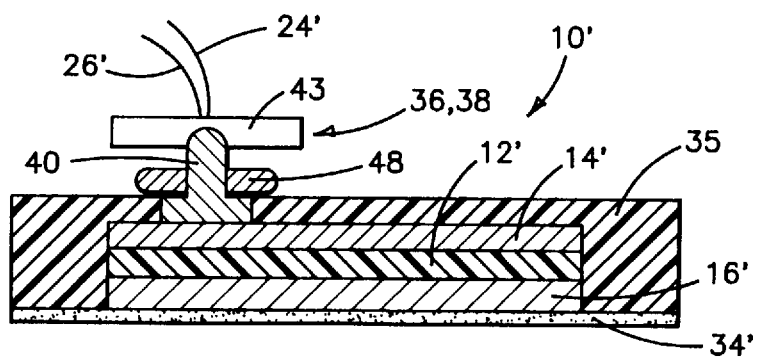
FIG. 3 is a cross sectional view of a second embodiment of a sensing device in accordance with the present invention.
Figure 4:
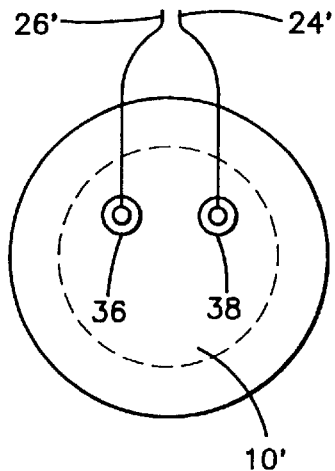
FIG. 4 is a top view of the sensing device of FIG. 3.

An alternate embodiment of a sensing device 10' in accordance with the present invention is illustrated in FIGS. 3 and 4. As before, the sensing device 10' comprises a thin film piezoelectric transducer material layer 12', metal coating layers 14' and 16', and adhesive layer 34' on the subject side of the sensing device.

The sensing device of FIGS. 3 and 4 differs from the device of FIG. 1 in two respects. The first is that the sensor diaphragm formed by the polymer transducer material layer 12' and the metal coating layers 14' and 16' is supported by a backing 35 of at least one of a polymer foam material and a molded polymer material. The backing 35 is preferably attached by adhesive to the sensor diaphragm in such a way that the diaphragm is in a slight amount of tension when at rest. As before, this aids the diaphragm in its sensitivity to any minute amount of acoustic or vibratory excitation. The backing and adhesive may be pliable and of such a durometer (hardness and spring rate) that they allow the diaphragm to conform to the flesh without distortion.

The second difference between the sensing devices of FIGS. 1 and 3 is the electrical connection between the leads 24' and 26' and the metal conductive layers 14' and 16'. In the embodiment of FIG. 3, the electrical connections are formed by quick connectors 36 and 38, one of which terminates the upper conductive coating layer and the other of which terminates the lower conductive coating layer. Quick connectors are used to provide a security lock so that the sensing device 10' can be used only with compatible type(s) of electrical leads. This helps to provide a measure of patient safety in that one cannot connect high voltage leads or ECG leads to the subject. Also, it insures that other types of incompatible or mismatched sensors are not used by mistake.

Figure 5:
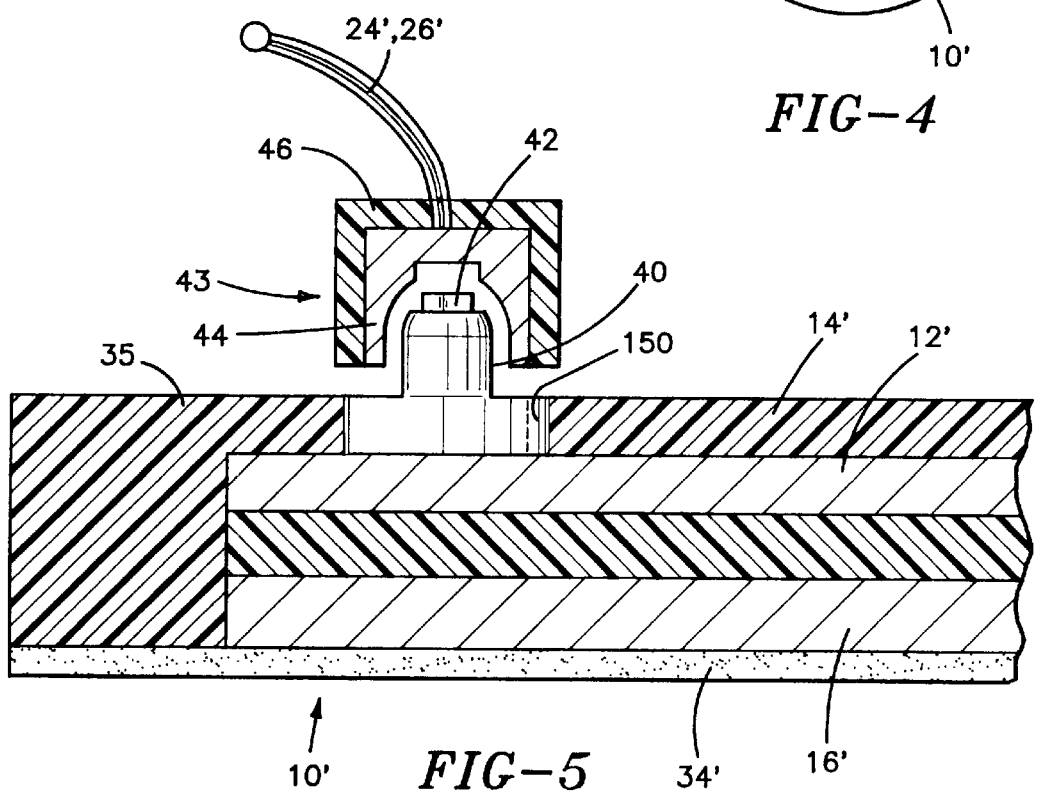
FIG. 5 is a cross sectional view of a first electrical connector which may be used with the sensing devices of the present invention.

FIG. 5 illustrates one type of quick connector which can be used with the sensor of FIG. 3. The connector includes a male portion 40 which is mounted on or electrically connected to one of the metallization layers 14'or 16'. The male portion 40 extends through the backing 35 and has a raised snap connector portion 42. The quick connector further includes a female portion 43 to which one of the leads 24' or 26' is electrically connected.

The female portion 43 has an electrical contact layer 44 formed from an electrically conductive metal or metal alloy and an outer non-conductive cover 46 formed from a molded polymer material or any other suitable electrically non-conductive material. As shown in FIG. 5, the layer 44 is shaped to conform to the shape of the male portion 40 and the raised snap connector portion 42. In this way, a secure connection can be made between the male and female portions.

As shown in FIG. 3, a sensor terminal connector 48 may be provided to insure that the backing 35 does not move relative to the male portion 40 of the quick connector. The connector 48 may be formed by a metal ring crimped onto the male portion 40 of the quick connector.

Figure 6A:
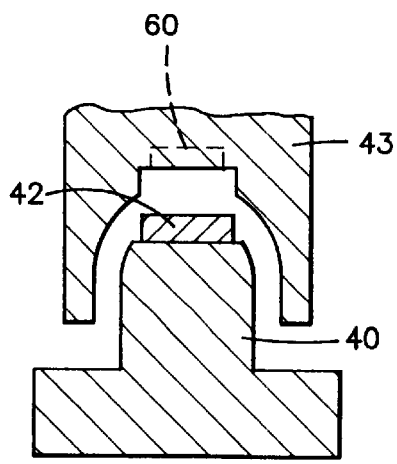
FIG. 6A is a cross sectional view of a second electrical connector which may be used with the sensing devices of the present invention.
Figure 6B:
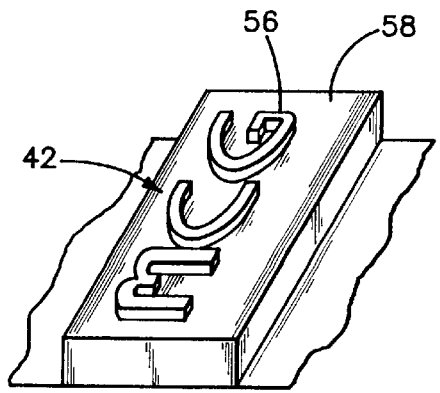
FIG. 6B is a top view of the male portion of the connector of FIG. 6A.

FIGS. 6A and 6B illustrate another quick connector device 36', 38' which may be employed with the sensing devices of the present invention. The quick connector device 36', 38' also has a male portion 40 and a female portion 43 of a construction identical to that of the connector device shown in FIG. 5. It differs however in that it includes a mechanical lock which consists of embossed metal letters 56 on the top surface 58 of the raised snap connector portion 42 and mating letters 60 formed in the female portion 43. This type of mechanical lock is particularly useful in insuring that non-compatible leads are not used with the sensing device of the present invention. While the mechanical lock has been illustrated using the letters "MCG", it should be recognized that the mechanical lock could be formed by any desired combination of embossed letters, numbers and symbols.

FIG. 7 illustrates a novel patch type sensing device 62 in which an array of four sensing devices 10 and 10' are embedded within or mounted to a relatively large adhesive patch formed from a compliant plastic material such as a compliant polymer foam material. A compliant plastic material is used for the patch so that the sensing device 62 may take the form of that portion of the subject's body over which it is to be placed. An adhesive layer (not shown) may be formed on the underside of the plastic material to insure a good connection between the subject and the sensing device(s). Alternatively, in a situation where the sensing devices 10 or 10' are embedded within the plastic material and have a lower surface in contact with the subject, the adhesive layer (not shown) may only be applied to the underside of the individual sensors in contact with the subject.

The patch sensing device 62 thus described is useful for picking up multiple acoustic outputs and for triangulating the excitation output signals so as to pinpoint the location and source of the acoustic output, e.g., from which human heart valve a murmur is emanating or from which artery or other blood flow passage/vessel a sound emanates. The four sensing devices 10, 10' can be positioned within or on the sensor patch material so that they cover the four heart valves of the subject. The sensing devices 10, 10' may have individual leads to a conditioning circuit or display device or may share common leads. If desired, ECG electrodes 64 may also be embedded within or mounted to the plastic material forming the patch sensing device.

While the sensing device 62 has been illustrated as having four sensing devices 10, 10', it can actually have any desired number of sensing devices. For example, the patch device 62 could have only two sensing devices, 10, 10'.

FIGS. 8 and 9 illustrate a unique bayonet connector 66 which may be used for the leads attached to the sensing devices 10 and 10'. The connector 66 includes a female portion 68 and a male portion 70. The female portion 68 preferably has an inner metal contact layer 72 for receiving a mating male contact and a molded plastic non-conductive cover 74. The male portion comprises a molded non-conductive cover portion 76 formed from a suitable plastic material and a male pin 78 formed from a suitable metal or metal alloy.

To insure that non-compatible leads are not utilized, the male pin 78 and the receptacle 80 within the female contact layer 72 are provided with mating shapes. For example, the male pin 78 may be provided with a tip 82 having a desired radius or curvature and an edge 84 which has a region 86 of different taper near the tip. For example, the taper angle $\beta$ of the edge portion 84 may be different than the taper angle $\alpha$ of the remainder of the pin. Of course, the receptacle 80 would be shaped to have an identical configuration so that the male pin would fit snugly therein.

Still another type of connector which may be employed with the sensing devices of the present invention is one in which an integrated circuit chip 150 is placed on the head of the sensing device. The chip may be used to accomplish a variety of tasks. For example, the chip may carry the sensor serial number and manufacturing lot code for FDA traceability. The chip may also carry the wave pattern of the dynamic response of the sensor so that the back end electronics recognize the sensor as a compatible device, thus providing system security. The sensor chip may have a code reflecting the diameter size of the sensor so as to let the back end electronics recognize it as a fetal sensor, infant/child sensor or an adult sensor. The various coded signals described above allow the sensor and back end electronics to proceed through an initialization sequence before normal communications will occur.

FIGS. 10 and 11 illustrate still another embodiment of a sensing device 10" in accordance with the present invention. This sensing device 10" has a sensing diaphragm formed by two layers 88 and 90 of thin polymer piezoelectric transducer material of the type previously discussed. The sensing device further includes metallization layers 92, 93, 94 and 95 and snap connector contacts 96 and 98 connected to respective ones of the metallization layers. Two of the metallization layers 92 and 95 are + layers, while the other two layers 93 and 94 are − layers. Each metallization layer may, if desired, have a layer of a polymer protective coating material theron. An adhesive layer 102 is formed between the metallization layers 92 and 95 to hold the two layers in a desired position and at a desired tension level. The adhesive which is used for the layer 102 preferably has insulative properties.

Each of the electrical contacts 96 and 98 is formed by a metal or metal alloy members held in place by a respective two part rivet 97. The electrical contacts 96 and 98 are connected to respective ones of the metallization layers by leads 108 and 110. The leads 108 and 110 may each be formed from a silver or carbon bearing conductive elastomer material. Air gaps 89 and 91 are provided to avoid short circuits between certain metallization layers and the leads.

The sensing device further includes an adhesive layer 100 on the subject side of the device and a stiffener 104 for acoustically isolating the sensing device from background noise and for holding the sensing diaphragm in tension. The stiffener 104 may be formed from any suitable plastic material and may be shaped to form an air gap 103 with the sensing diaphragm. The stiffener 104 also serves as a mechanical mounting for the connectors 96 and 98.

The process to make sensors of the type described herein starts with raw sheets 120 of PVDF piezoelectric film material. The film material is cleaned and mounted on a rotating drum in a vapor depostion machine. An ultrahigh vacuum is pulled on the chamber and aluminum, nickel, copper or alloys thereof are sputtered onto the film in thin layers 122. This process is repeated for both sides. Leads 123 and termination rings 125 may be formed during this step. Appropriate masking (not shown) can be done to keep the metallization off of non-conductive areas for design purposes. At this point, several processes can occur, but there is the option of having them occur downstream.

For example, to form a sensor similar to that shown in FIGS. 10 and 11, the sheets of metallized PVDF film material are provided with a layer of polymer protective coating. The sheets of metallized PVDF film material are also provided with a layer of double backed sticky adhesive applied to one side of the metallization after the protective coatings are applied. The protective coating serves to keep the adhesive from shorting out the metallization.

Figure 12:
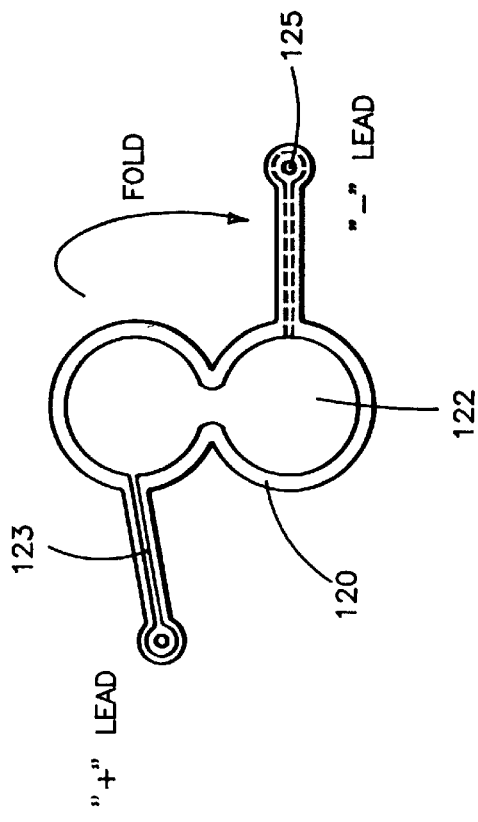
FIGS. 12–15 illustrate a process for making a sensor in accordance with the present invention.

At this point, the sheets of processed PVDF material with metallization, protective coating and adhesive can be die cut to fabricate the substantially dog-boned shaped pattern of sensors and leads shown in FIG. 12 which will be folded over to form a double layered sensor (more than two layers can be used if desired). Once the die cut process is completed, the sensor diaphragms can be prepared.

Figure 13:
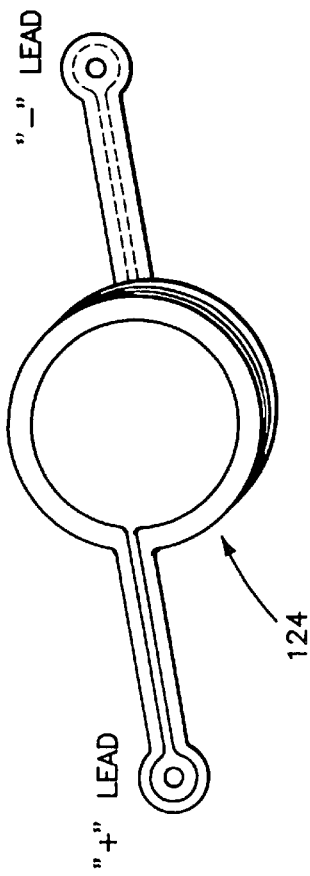

The dog bone shaped pieces must be cleaned of all debris and contaminants. A thin layer of anerobic adhesive is applied to the side with no adhesive. As shown in FIG. 13, the sensor is folded over to make the double layered sensor 124 and the diaphragms are sandwiched in a fixture to bond them tightly. The whole fixture is then placed in a vacuum chamber (not shown) with ultra high vacuum to outgas all air and gas bubbles from the adhesive. This creates an integral and substantially uniform bond between sensor layers so that the dynamic response of the sensor is linear and proportional across the entire face of the sensor. The diaphragms are then removed from the fixturing and cleaned.

Figure 14:
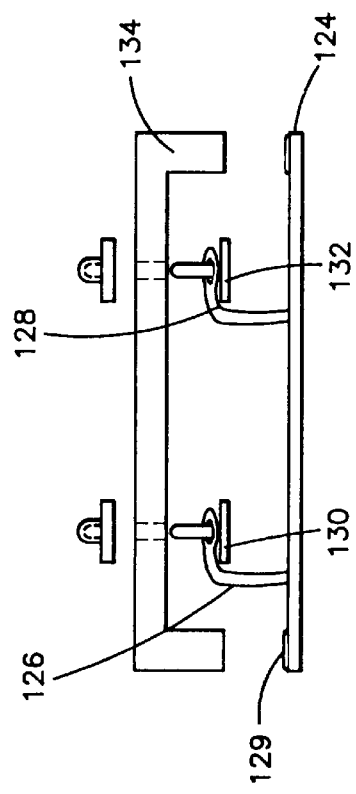
Figure 15:
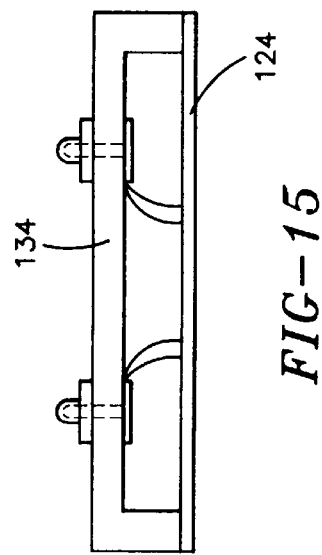

The next step is to assemble the diaphragms to the stiffener/electrode assembly. As shown in FIG. 14, the leads 126, 128 of the sensor diaphragms are placed into the rivet like connectors 130, 132 of the snap lead connectors. The snap connectors are crimped in place onto the stiffener 134 as they capture and make electrical contact with the diaphragm leads. A thin layer of anerobic adhesive 129 is applied to the upper rim of the diaphragm and the diaphragm is placed against the lower rim of the stiffener 134. A special fixture is attached to the diaphragm/stiffener assembly during adhesive curing. This fixture has an expanding collet (not shown) with a rubber surface which presses against the diaphragm as it expands and, by virtue of the friction between the rubber and diaphragm, the collet acts to expand the diaphragm uniformly in an outward radial direction, and places the diaphragm in a slight degree of tension during adhesive curing. The entire fixture is placed in a vacuum chamber under ultrahigh vacuum during curing. The process of holding the diaphragm in tension and curing in a vacuum acts to have the diaphragm remain in tension after curing so as to remove all rimples and creases from the thin film so the sensor has a uniform and linear dynamic response across the entire diameter.

The assembly is then tested for uniform and radial dynamic response using a heart sound simulator with known amplitude, frequency and timing characteristics. It should be noted that the application of protective coatings and adhesive can be done before or after die cutting of film, but the process is made easier by processing uncut sheets of film.

A sensing device has been described which is capable of capturing cardiac output and acoustic output from arterial blood flow off the chest and appendages. The sensing device(s) of the present invention can be mounted to auscultation points on the chest and the neck. They can also be used on any pulse capturing point on the body, including the abdomen of a pregnant woman for capturing fetal heart sounds. The sensing device(s) can be used with adults, infants, small children and animals. The sensing device(s) of the present invention are flexible enough to conform to flesh in such a way that they essentially couple with the flesh and become part of the flesh for maximum transfer of energy. Still further, the sensing device(s) of the present invention are sufficiently sensitive to detect turbulent blood flow due to blockages in major arteries and veins deep within the body of a subject.

Another advantage to the sensing device(s) of the present invention is that they can be sterilized for one use. After such use, they can be discarded. This allows the sensing device(s) to be used in operating rooms, intensive care units, and other environments where sterility is critical. Alternatively, the sensing device(s) may be reused if so desired.

The sensing device(s) of the present invention may be quickly connected and disconnected from electrical leads and thus may easily be discarded after one or more uses and replaced by another sensing device.

Still another advantage of the sensing device(s) of the present invention is that they have excellent frequency response and sensitivity which can be tailored to low frequencies (below 4000 Hz) and low amplitude (less than 5 dB) signals from the heart and major arteries.

Yet another advantage is that the sensing device(s) can come in a wide variety of size designed to maximize acoustic localization. For example, the device(s) may have a diameter of about one-half inch for adults and a diameter of about one quarter inch for children.

While it is preferred not to apply an excitation voltage to the polymer film material for picking up the acoustic and/or vibratory energy, such voltages may be applied if desired.

It is apparent that there has been provided in accordance with this invention a disposable sensing device with contaneous conformance which fully satisfies the objects, means and advantages set forth hereinbefore. While the invention has been described in combination with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

What is claimed is:

1. A patch sensing device for picking up multiple acoustic output signals in a subject's anatomy and for triangulating the acoustic output signals so as to pinpoint a location and source of the acoustic output signals in the subject's anatomy,
   wherein the acoustic output signals have a location and source in the subject's anatomy,
   wherein said patch comprises a sheet of compliant material which can be conformed to a shape of a surface of a portion of the subject's anatomy above the subject's heart valves,
   wherein the sheet comprises at least two sensors in laterally spaced apart association therewith,
   wherein each of said laterally spaced apart sensors has a diaphragm formed from a piezoelectric polymer transducer material, and
   wherein said laterally spaced apart sensors are positioned to cover the subject's heart valves when the patch is conformed to the shape of the surface of the portion of the subject's anatomy above the subject's heart valves.

2. The sensing device of claim 1 further comprising:
   ECG electrodes associated with said patch material.

3. The sensing device of claim 1 further comprising:
   four sensors associated with said patch; and
   said four sensors being positioned substantially over the subjects' heart.

* * * * *